United States Patent [19]

James

[11] 4,361,157

[45] Nov. 30, 1982

[54] METHOD OF CURLING NEGROID HAIR WITHOUT ROLLERS

[76] Inventor: Odie R. James, 3817 Fannin, Houston, Tex. 77004

[21] Appl. No.: 198,479

[22] Filed: Oct. 20, 1980

Related U.S. Application Data

[63] Continuation of Ser. No. 17,113, Mar. 5, 1979, abandoned.

[51] Int. Cl.$^3$ .............................................. A45D 7/00
[52] U.S. Cl. ...................................................... 132/7
[58] Field of Search .......... 132/7; 424/DIG. 2, 70–71

[56] References Cited

U.S. PATENT DOCUMENTS

| | | | |
|---|---|---|---|
| 2,624,347 | 1/1953 | Melaro | 132/7 |
| 2,719,813 | 10/1955 | Haefele | 167/87.1 |
| 2,865,811 | 12/1958 | Roesch | 132/7 |
| 3,063,908 | 11/1962 | Kalopissis | 132/7 |
| 3,470,887 | 10/1969 | Kremer et al. | 132/7 |
| 3,654,936 | 4/1972 | Wajaroff | 132/7 |
| 3,757,804 | 9/1973 | Kalopissis et al. | 132/7 |
| 3,805,809 | 4/1974 | Zeffren et al. | 132/7 |
| 3,809,098 | 5/1974 | Anderson | 132/7 |
| 3,823,232 | 7/1974 | Salerne | 132/7 |
| 3,880,174 | 4/1975 | Wajaroff | 132/7 |
| 3,892,246 | 7/1975 | Woodard | 132/7 |
| 3,935,868 | 2/1976 | Zeffren et al. | 132/7 |
| 3,964,499 | 6/1976 | Wajaroff et al. | 132/7 |
| 3,972,336 | 8/1976 | Nowak, Jr. et al. | 132/7 |
| 3,973,574 | 8/1976 | Minagawa | 132/7 |
| 4,038,995 | 8/1977 | Edelberg et al. | 132/7 |

OTHER PUBLICATIONS

Ultra Sheen Permanent Creme Relaxer Instructions.

*Primary Examiner*—G. E. McNeill
*Attorney, Agent, or Firm*—Neal J. Mosely

[57] ABSTRACT

A method is disclosed for producing soft, gentle waves in negroid hair without use of curlers. Negroid hair, in the naturally kinky state is first treated with hair straightening chemicals to establish a standard reference time for carrying out a hair straightening treatment. With this reference time determined, it is then possible to treat this hair, or other similar hair in accordance with this process.

An untreated negroid hair, in the naturally kinky state is wet thoroughly and hair straightening chemicals applied thereto and allowed to set for a period of 10–15 minutes, corresponding to about 70–90% of the time of exposure of the hair to the chemicals required for straightening the hair. The precise time allowed for the treatment depends on the coarseness of the hair. The hair is combed out and stretched in sections during the time of exposure to the hair-straightening chemicals. Next, the hair is shampooed using a shampoo containing chemicals for neutralizing the hair straightener. The hair is then rinsed and set and a hair softener applied. The hair is then allowed to dry without heat or blowing. The method produces soft gentle waves without use of curlers and is effective in curling hair in periods of time as short as 25–30 minutes.

7 Claims, No Drawings

METHOD OF CURLING NEGROID HAIR WITHOUT ROLLERS

This application is a continuation of Ser. No. 17,113, filed Mar. 5, 1979, now abandoned.

BACKGROUND OF THE INVENTION

1. Field of the Invention

This invention relates to methods of treatment of naturally kinky hair, particularly Negroid hair and, more particularly, relates to methods of producing soft, gentle curls in such hair.

2. Brief Description of the Prior Art

The treatment of Negroid hair requires very special attention as a result of the particular characteristics of such hair. Negroid hair is naturally kinky or very tightly curled. There are a variety of approaches to the handling of Negroid hair depending upon the attitude of particular individuals. Some Negroes or blacks prefer to have their hair straightened. Some like to have their hair cut and handled in a way which retains its natural kinkiness or tight curl. Others like to have their hair straightened in a very full manner producing the Afro hairdo. Still others like to have their hair straightened and then curled into soft, gentle curls.

When Negroid hair has been curled in the past, it has been necessary to first straighten the hair by chemical or heat setting techniques and then subjecting the straightened hair to a curling process using rollers and heat or chemical treatment to produce the desired curl. This procedure has required treatments of up to several hours and has required the hair to be maintained on curlers during treatment and drying to produce the desired curl and has also required the use of curlers for resetting between treatments by the barber or the beautician.

There are a large number of U.S. patents which deal with hair waving and hair straightening methods. Patents which have some relevance to the subject invention, are abstracted briefly below. These patents are considered relevant either in the method steps or in providing background or setting for the subject invention or in disclosing chemicals which are used in hair straightening and hair curling methods.

Pileggi, U.S. Pat. No. 2,377,808, discloses a method of curling hair which involves wetting, washing and rinsing hair cut to accept natural curl and followed by a slow dry at 95°–110° F.

Roesch, U.S. Pat. No. 2,865,811, discloses a process of straightening Negroid hair. The hair is shampooed with soap and thioglycolic acid, washed and rinsed, partially dried at 38° C. for 5–10 minutes and then dried with a hot comb at 75°–130° C.

Kalopissis, U.S. Pat. No. 3,063,908, discloses permanent waving using mercaptoamides as a treating reagent.

Kremer, U.S. Pat. No. 3,470,887, discloses a hair straightening process applying a water soluble acidic (pH 1.5–5) cream then a water soluble cream containing a thiol at pH 8.5–9.5.

Wajaroff, U.S. Pat. No. 3,654,936, discloses a hair straightening process by (1) applying a keratine softener, (2) washing out softener, (3) treating with a swelling agent and (4) combing or mechanically straightening.

Kalopissis, U.S. Pat. No. 3,757,804, discloses a hair conditioning and waving process wherein the hair is set on rollers and dried under a hood at 45° C.

Zeffren, U.S. Pat. No. 3,805,809, discloses a curling process using a persulfate treatment shampoo, winding on curlers, and room temperature drying for an extended period of time.

Anderson, U.S. Pat. No. 3,809,098, discloses a curling or straightening process using a persulfate treatment at pH 5–10 and EDTA.

Wajaroff, U.S. Pat. No. 3,880,174, discloses a treatment for curling or straightening hair involving use of an alkaline treating material, mercaptide hardening, and requires the hair to be set on rollers.

Wajaroff, U.S. Pat. No. 3,964,499, discloses a straightening or curling process which uses a fulfite-containing detergent at pH 6–7.5, lauryl alcohol sulfonates as a surfactant, and uses rollers for setting.

Nowak, U.S. Pat. No. 3,972,336, discloses the use of sulfonated polymers in curling or straightening hair.

Minagawa, U.S. Pat. No. 3,973,574, discloses a process for waving and straightening hair by use of an alkaline treatment and a chelating agent.

Edelberg, U.S. Pat. No. 4,038,995, discloses a hair treatment method using a composition containing ammonium or sodium sulfate or bisulfite and a quaternary ammonium salt of a fatty acid and requires the use of curlers.

SUMMARY OF THE INVENTION

It is one object of this invention to provide a new and improved method for producing soft, gentle waves in Negroid hair.

Another object of this invention is to provide an improved method for waving Negroid hair without the use of curlers.

Still another object of this invention is to provide an improved method for producing soft, gentle waves in Negroid hair in very short periods of time.

Still another object of this invention is to provide an improved method for waving Negroid hair wherein the hair does not require rewaving or the use of curlers between normal times of treatment by the barber or beautician.

Other objects of this invention will become apparent from time to time throughout the specification and the claims as hereinafter related.

A method of producing soft, gentle waves in Negroid hair involves a treatment which does not require the use of curlers or of drying at elevated temperatures. Untreated Negroid hair, in the natural kinky state, is first treated with alkaline hair straightening chemicals to carry out a partial straightening process. The hair is first treated with hair-straightening chemicals to establish a standard reference time for carrying out a complete hair-straightening treatment. With this standard reference time determined, it is then possible to treat this hair, or other Negroid hair of a similar degree of fineness or coarseness in accordance with this invention.

In carrying out this method, in untreated Negroid hair, in the naturally kinky state, is wet thoroughly and strongly alkaline hair-straightening chemicals are applied. The hair, with the chemicals applied thereto is allowed to set for a period of 10–15 minutes which corresponds to about 70–90% of the time of exposure of the hair to such chemicals which would be required for a complete straightening of the hair. The precise time allowed for treatment depends on the coarseness of the hair and is shorter for fine hair and longer for coarser hair. During the time of exposure of the hair to the straightening chemicals, the hair is combed out and stretched in sections. The hair is then shampooed using a shampoo containing chemicals for neutralizing the hair straightener. Afterwards, the hair is rinsed and a hair softener applied. The hair is then allowed to dry without heating or blowing. This method produces soft, gentle waves in the hair without the use of curlers and the method is effective in curling hair in periods of time as short as 25-30 minutes, as compared to several hours required where hair is completely straightened and then subjected to a more conventional curling process.

DESCRIPTION OF THE PREFERRED EMBODIMENTS

The process used to straighten the hair of Negroes is essentially the same process used in curling and permanent waving normally straight hair. The procedure involves first wetting the hair and applying a chemical to the hair which breaks down the chemical structure and allows it to be formed or shaped. In the case of initially straight hair, the hair is treated with such a chemical and wound on rollers and then treated with a neutralizing agent and shampooed and rinsed. If the hair is to be straightened, as in the case of Negroid hair, it is combed out and stretched while in the treated condition. In the past, it has been difficult to treat Negroid hair to produce long, relatively loose curls without going through a complete straightening procedure and subsequently, treating the hair to provide the desired permanent curls or waves. Such a procedure has involved the use of curlers and forced heated air drying and has been very time consuming, requiring up to several hours.

In the preferred embodiment of this invention, Negroid hair is formed into soft, relatively loose curls in about thirty minutes without going through a complete straightening procedure and without the use of curlers or forced, heated air drying.

In this method, the Negroid hair, in its untreated, kinky state, is wetted thoroughly and a hair straightening chemical applied. Usually, the hair straightening chemical will be a strongly alkaline reagent. The hair which has been treated with the alkaline straightening material, is allowed to set for a period of 10-15 minutes according to the coarseness of the hair. This setting time represents about 70-90% of the time of exposure to the hair straightening chemicals required for a complete straightening process. The precise time is determined by initially testing Negroid hair of different degrees of fineness or coarseness to determine the normal exposure time to the chemicals required for complete straightening.

During the time that the hair is exposed to the alkaline straightening material, it is combed out and stretched in sections. The hair is then shampooed using a shampoo containing neutralizing chemicals to neutralize and terminate the effect of the alkaline straightening reagents. The hair is then rinsed and, if desired, a hair softener is applied. The hair is allowed to dry without heat or blowing and produces soft, loose curls in 25-30 minutes, as compared to 3-4 hours in the case of prior art methods.

The following non-limiting examples are illustrative of the scope of this invention.

EXAMPLE ONE

Treatment of Negroid hair in accordance with this invention was carried out using a commercially available hair straightener product marketed under the trademark Ultra Sheen by Johnson Products Company, Inc., Chicago, Ill. This product has three components which are used in different stages of treatment, viz, a straightener or relaxer, a neutralizer-shampoo, and a rinse-set composition. The straightener or relaxer includes the following ingredients: water, petrolatum, cetyl alcohol, sodium hydroxide, oleyl alcohol, PEG-75, lanolin, OLETH-20, stearic acid, sodium lauryl sulfate, and hydrolyzed animal protein. It should be noted that the composition contains 2.2% wt. of sodium hydroxide and care is required in applying it to the hair to avoid contact with any breaks or abrasions in the scalp and also to avoid getting it in one's eyes. The neutralizer shampoo has the following composition: water, ammonium lauryl sulfate, cocamide DEA, sodium chloride, cocomidopropylamine oxide, citric acid, imidazolidinyl urea, disodium EDTA, methylparaben and benzophenone-4. The rinse-set composition has the following ingredients: water, oleamide MIPA, isopropyl alcohol, ceteareth-20, quaternium-18, lauryl pyridinium chloride, methylparaben, acetic acid, and 2-Bromo-2-nitropropane-1, 3-diol.

When this material is used in straightening Negroid hair, the straightener or relaxer is applied to hair which has been pre-wet and is allowed to set on the treated hair for a period of about 13-20 minutes depending upon the coarseness of the hair. Fine hair is treated for about 13 minutes. Medium is treated for about 15 minutes. Coarse hair is treated for about 18-20 minutes. These application times may be determined experimentally, according to the coarseness of the hair and are also in the range of time recommended by the manufacturer. During a period of time that the hair is being straightened, it is combed out and stretched. At the end of the specified time, the hair is washed with the neutralizer-shampoo composition which neutralizes most of the alkalinity in the straightener composition. Finally, the hair is rinsed with warm water to remove the excess alkalinity and the rinse-set material is applied to cause the hair to set in a complete straightened condition. A softener may be applied at the end of the treatment if needed.

In the preparation of softly curled hair, according to this invention, the untreated, naturally kinky, Negroid hair is first wet thoroughly and then the straightener composition is applied for a period of time ranging from about 10-15 minutes according to the coarseness of the hair. The time selected represents about 70-90% of the time of exposure of the hair to the straightener composition required for a complete straightening of the hair. During the time that the hair is being treated with the straightener composition, it is combed out in sections, and stretched. The stretching operation is strictly by comb and does not require the use of curlers or other tensioning devices.

At the end of the period of exposure to the straightener composition, and after the hair is thoroughly combed out and stretched, the hair is shampooed using the neutralizer-shampoo composition. The neutralizer-shampoo is diluted with water and is effective to wash out the straightener composition from the hair and neutralizer the strongly alkaline material absorbed therein. The hair is then rinsed, using the rinse-set composition diluted further with water. This composition washes out the remainder of the straightener composition and completes the neutralization and setting of the hair in a partially straightened condition. A hair softener is then applied, if desired. The hair is then allowed to dry without heat or blowing and without the necessity of winding on curlers or rollers. The hair may be cut and shaped, while wet, during this final passive drying step.

This procedure is effective to convert a naturally kinky Negroid hair from the kinky state to long, soft, gentle waves or curls in a period of time of about 25–30 minutes and, as noted above, does not require blowing with heated air. The soft, gentle waves produced by this method will stay in the hair through repeated washing without the necessity of recurling on curlers or rollers and needs to be treated further only when the roots have grown out appreciably.

The method or procedure described in this example is effective in producing soft, gentle waves in Negroid hair in short periods of time provided that the specified sequence of treating steps is followed. Other types of hair straightening chemicals may be used and the desired waves obtained providing that the sequenced steps and the time for treatment is followed as in this example. The following examples illustrate the application of this method or procedure to the production of soft, gentle waves in Negroid hair in other types of hair-straightener compositions.

EXAMPLE TWO

The treating solution is prepared consisting of about 9% wt. of mercapto acetamide in water. The solution is brought to pH 9.0 with acqueous ammonia. This solution is then neutralized to pH 7.0 with dilute acetic acid.

Naturally kinky hair is wet thoroughly and the mercapto acetamide treating solution is applied thereto. The solution is allowed to set on the hair for a period of 10–15 minutes at room temperature, depending upon the coarseness of the hair. The period of exposure to the treating solution is greatest for coarse hair and least for fine hair. This treating time compares with a contact time of 15–25 minutes at room temperature if the hair is to be completely straightened. During the time that the hair is being treated with a mercapto acetamide treating solution, it is combed out and stretched in sections.

Next, the hair is shampooed with a shampoo containing an oxidizing agent, such as sodium peroxide or hydrogen peroxide. This oxidizing agent neutralizes, i.e., inactivates, the mercapto acetamide which was used to soften the hair. The hair is then rinsed and, if desired, a hair softener may be applied. Finally, the hair is allowed to dry at room temperature, without heat or blowing, and without the necessity of being put up on rollers. This treatment produces a soft, gentle wave in a period of time as short as 25–30 minutes, as compared to 3–4 hours in the case of prior art processes where the hair would have to be completely straightened and then subjected to permanent waving.

EXAMPLE THREE

A naturally kinky hair, such as a Negroid hair, is thoroughly wet with an acid rinse. The hair is then treated with a hair softening cream consisting of a mixture of thioglycolic acid and thioglycerol emulsified in water. The softener is allowed to remain on the hair for a period of 10–15 minutes, which represents a period of about 70–90% of the time required for a thorough straightening of the hair. During this softening period, the hair is combed out straight in sections.

After the softening period of 10–15 minutes, the hair is washed with a surfactant solution containing dilute hydrogen peroxide as a neutralizer for the thiol hair softener. The hair is then rinsed out and allowed to dry at room temperature without blowing and without being stretched on curlers.

The hair treated in this manner is in the form of soft, gentle waves and does not require the use of curlers. The total treating time is in the range of about 25–30 minutes, as compared to 3–4 hours for prior art processes.

EXAMPLE FOUR

A hair straightening cream is prepared by emulsifying cetyl alcohol, paraffin oil, and ethoxylated (20) oleyl alcohol with aqueous ammonium thiolglycolate. The straightening composition is applied to naturally kinky hair, e.g., Negroid hair, for a period of 10–15 minutes. The treatment time corresponds to about 70–90% of the time required for thorough straightening of the hair. The application of straightening material follows an initial wetting or rinsing or shampooing treatment, as desired. During the straightening period, the hair is combed in sections and partially straightened. The hair is then shampooed with any conventional shampoo having a small amount of hydrogen peroxide added thereto. The hydrogen peroxide in the shampoo functions as a neutralizing agent for the thiol straightening material.

After the neutralizing treatment, the hair is rinsed and allowed to dry at room temperature. No curlers are required. The treatment produces soft, gentle waves in the hair after a total treating time of 25–30 minutes as compared to 3–4 hours for prior art processes.

EXAMPLE FIVE

A naturally kinky, e.g., Negroid, hair is wet down thoroughly and treated with a straightening solution containing about 1% sodium hydroxide and 0.5% polyoxyethylene lauryl ether. The treating solution is allowed to remain on the hair for a period of 10–15 minutes, which represents about 70–90% of the time required for complete straightening of naturally kinky hair, depending upon the coarseness or fineness of hair.

During the period of time that the hair is exposed to the straightening solution, the hair is combed in sections. The hair is then rinsed and shampooed again with a shampoo containing an acidic material to neutralize the sodium hydroxide. The hair is finally rinsed again and, if desired, a softening material is added.

At the conclusion of the treatment, the hair is allowed to dry at room temperature without blowing and without being put up on curlers. This treatment is effective to produce soft, gentle curls in the hair without the necessity of using curlers and in a very short treatment time. As in the other examples, this process is effective to produce soft, gentle curls in the hair in a period of about 25–30 minutes as compared to several hours using prior art treatment methods.

While this invention has been described fully and completely with special emphasis upon several preferred embodiments, it should be understood that within the scope of the appended claims, the invention may be practiced otherwise than as specifically described herein.

I claim:

1. A method of producing soft, relatively loose curls in naturally kinky hair without use of curlers or rollers comprising:

wetting the hair thoroughly, applying thoroughly and uniformly to the hair a solution of a chemical reagent for straightening the hair, allowing said straightening reagent to remain on the hair for a predetermined period of about 70–90% of the time required for complete straightening of the hair, said predetermined period of time varying according to the degree of coarseness of the hair as determined empirically by measuring the time required for completely straightening fine or medium or coarse hair completely, said predetermined period of time being about 13 minutes for fine hair, about 15 minutes for medium hair, and about 18–20 minutes for coarse hair, combing the hair out straight during the time that said chemical hair-straightening reagent remains thereon, at the end of the aforementioned time, before the time that the hair is fully straightened, shampooing and rinsing the hair with a shampoo and rinse, at least one of which contains a chemical reagent for neutralizing said hair straightening reagent and setting said hair, the steps prior to this point taking about one-half hour, and allowing said hair to dry in the combed out state without application of forced heated air or the use of curlers or rollers to yield soft curls.

2. A method according to claim 1 in which said hair-straightening reagent contains sufficient sodium hydroxide to soften the hair and said neutralizing and setting reagent comprises an acid for neutralizing the same.

3. A method according to claim 1 in which said hair-straightening reagent contains a thiol-type hair waving or straightening compound and said neutralizing and setting reagent comprises an oxidizing material to oxidize and neutralize the effect of said thiol compound.

4. A method according to claim 1 in which the hair, after treatment with said hair-straightening reagent for said predetermined time, is shampooed with a surfactant solution containing a neutralizing reagent and then rinsed with a solution containing a setting reagent.

5. A method according to claim 4 in which
said hair-straightening reagent comprises sodium hydroxide,
said shampoo comprises a detergent or surfactant containing an acid, and
said rinse/setting composition comprises a mixture of surfactants and an acid.

6. A method according to claim 3 in which:
said thiol-type hair straightening reagent consists of a mercaptoamide, thioglycerol, thioglycolic acid, or a thioglycolate salt.

7. A method according to claim 5 in which:
said hair-straightening reagent comprises water, petrolatum, cetyl alcohol, sodium hydroxide, oleyl alcohol, PEG-75, lanolin, OLETH-20, stearic acid, sodium lauryl, sulfate and hydrolized animal protein,
said neutralizer/shampoo comprises water, ammonium lauryl sulfate, cocamide DEA, sodium chloride, cocoamidopropylamine oxide, citric acid, imidazolidinyl urea, disodium EDTA, methyl paraben and benzophenone-4, and
said rinse/set comprises water, oleamide MIPA, isopropyl alcohol, ceteareth-20, quaternium-18, lauryl pyridinium chloride, methylparaben, acetic acid and 2-bromo-2-nitropropane-1, 3-diol.

* * * * *